United States Patent
Li et al.

(10) Patent No.: US 12,021,555 B2
(45) Date of Patent: Jun. 25, 2024

(54) IMPLANTABLE MEDICAL DEVICE AND METHOD FOR MANAGING A PHYSICAL LAYER UTILIZED DURING A WIRELESS CONNECTION

(71) Applicant: Pacesetter, Inc., Sylmar, CA (US)

(72) Inventors: Perry Li, Arcadia, CA (US); Jeffery Crook, Belmont, CA (US); Souvik Dubey, Woodland Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 195 days.

(21) Appl. No.: 17/085,017

(22) Filed: Oct. 30, 2020

(65) Prior Publication Data

US 2022/0140854 A1    May 5, 2022

(51) Int. Cl.
*H04B 7/00*    (2006.01)
*A61N 1/372*    (2006.01)
(Continued)

(52) U.S. Cl.
CPC ......... *H04B 1/401* (2013.01); *A61N 1/37276* (2013.01); *H04B 1/3827* (2013.01);
(Continued)

(58) Field of Classification Search
CPC .... H04B 1/401; H04B 1/3827; H04B 7/2603; H04B 2201/71346; H04B 1/707;
(Continued)

(56) References Cited

U.S. PATENT DOCUMENTS 7,406,710 B1 *    7/2008    Zellner ............... H04L 65/1069
                                                                                                             713/169
7,583,649 B1 *    9/2009    Bagchi .................... H04L 49/90
                                                                                                             455/450

(Continued)

FOREIGN PATENT DOCUMENTS

EP             2426865 A2      7/2012

OTHER PUBLICATIONS

Extended European Search Report for corresponding EP Application No. 21179178.5-1122 dated Dec. 16, 2021.

*Primary Examiner* — Stephen M D Agosta
(74) *Attorney, Agent, or Firm* — Dean D. Small; The Small Patent Law Group, LLC

(57) ABSTRACT

An implantable medical device, external device and method for managing a wireless communication are provided. The IMD includes a transceiver configured to communicate wirelessly, with an external device (ED), utilizing a protocol that utilizes multiple physical layers. The transceiver is configured to transmit information indicating that the transceiver is configured with first, second, and third physical layers (PHYs) for wireless communication. The IMD includes memory configured to store program instructions. The IMD includes one or more processors configured to execute instructions to obtain an instruction designating one of the first, second and third PHY to be utilized for at least one of transmission or reception, during a communication session, with the external device and manage the transceiver (Continued)

to utilize, during the communication session, the one of the first, second and third PHY as designated.

23 Claims, 4 Drawing Sheets

(51) Int. Cl.
  *H04B 1/3827* (2015.01)
  *H04B 1/401* (2015.01)
  *H04B 7/26* (2006.01)
  *H04L 1/00* (2006.01)

(52) U.S. Cl.
  CPC ......... *H04B 7/2603* (2013.01); *H04L 1/0002* (2013.01); *H04L 1/0009* (2013.01); *H04L 1/0017* (2013.01); *H04L 1/0025* (2013.01); *H04L 1/0035* (2013.01); *H04B 2201/71346* (2013.01)

(58) Field of Classification Search
  CPC .................. H04B 1/1036; H04B 1/709; H04B 2201/70715; A61N 1/37276; A61M 2205/3303; A61M 2205/502; A61M 2205/581; H04L 1/0002; H04L 1/0009; H04L 1/0017; H04L 1/0025; H04L 1/0035; H04L 27/2627; H04L 27/2649; H04L 1/0003; H04L 27/2017; A61B 5/14532; A61B 5/0004; A61B 5/14503; A61B 5/0031; A61B 5/7475; G16H 40/67; G16H 40/63; G16H 20/17; G16H 40/40; G16H 50/50; G16H 10/40; G01N 27/3273; G01N 27/3275; G01N 33/66; H04W 12/06; H04W 12/02; H04W 12/033; H04W 4/80; H04W 4/90; H04W 64/00; H04W 88/06; H04W 12/79; H04H 20/59; H04J 11/00; H04M 1/725; H04M 7/006

See application file for complete search history.

(56) References Cited

U.S. PATENT DOCUMENTS

| | | | |
|---|---|---|---|
| 8,554,333 B2 | 10/2013 | Wu et al. | |
| 8,923,773 B1 | 12/2014 | Gitlin et al. | |
| 9,288,614 B1* | 3/2016 | Young | H04W 76/14 |
| 9,408,147 B2 | 8/2016 | Polo et al. | |
| 9,813,189 B2* | 11/2017 | Chou | H04L 27/0008 |
| 10,182,336 B1* | 1/2019 | Stockton | A61N 1/37252 |
| 11,083,372 B2* | 8/2021 | Thakur | A61B 5/686 |
| 2003/0114898 A1* | 6/2003 | Von Arx | A61N 1/37223 |
| | | | 607/60 |
| 2003/0216135 A1* | 11/2003 | McDaniel | H04K 3/22 |
| | | | 455/410 |
| 2004/0030260 A1* | 2/2004 | Arx | A61N 1/37223 |
| | | | 600/549 |
| 2004/0032882 A1* | 2/2004 | Kane | H04L 67/04 |
| | | | 370/477 |
| 2006/0160534 A1* | 7/2006 | Jung | H04B 1/0483 |
| | | | 455/423 |
| 2006/0161222 A1* | 7/2006 | Haubrich | G16H 40/67 |
| | | | 607/32 |
| 2006/0241701 A1* | 10/2006 | Markowitz | A61N 1/39622 |
| | | | 607/5 |
| 2006/0287693 A1* | 12/2006 | Kraft | A61N 1/37229 |
| | | | 607/60 |
| 2007/0129045 A1* | 6/2007 | Aerrabotu | H04W 52/0277 |
| | | | 455/343.5 |
| 2007/0180047 A1* | 8/2007 | Dong | A61B 5/117 |
| | | | 600/300 |
| 2008/0086176 A1* | 4/2008 | Ofek | A61N 1/37211 |
| | | | 607/17 |
| 2008/0149659 A1* | 6/2008 | Dishongh | G16H 20/13 |
| | | | 221/3 |
| 2008/0240070 A1* | 10/2008 | Feher | H04W 64/00 |
| | | | 370/347 |
| 2008/0281585 A1* | 11/2008 | Feher | H04M 11/04 |
| | | | 370/347 |
| 2009/0016286 A1* | 1/2009 | Fajardo | H04W 36/005 |
| | | | 370/329 |
| 2009/0043360 A1* | 2/2009 | Doerr | A61N 1/37264 |
| | | | 607/59 |
| 2009/0247187 A1* | 10/2009 | Feher | H04J 11/00 |
| | | | 455/456.1 |
| 2010/0260679 A1* | 10/2010 | Shachar | G01N 33/5438 |
| | | | 424/9.1 |
| 2010/0297941 A1* | 11/2010 | Doan | G08C 17/02 |
| | | | 455/41.2 |
| 2010/0317289 A1* | 12/2010 | Desai | H04B 17/318 |
| | | | 455/41.2 |
| 2012/0119902 A1* | 5/2012 | Patro | H04W 52/0238 |
| | | | 340/502 |
| 2012/0128034 A1* | 5/2012 | Feher | H04J 11/00 |
| | | | 375/E1.033 |
| 2012/0191147 A1* | 7/2012 | Rao | G16H 20/17 |
| | | | 607/3 |
| 2012/0203076 A1* | 8/2012 | Fatta | A61B 5/681 |
| | | | 600/300 |
| 2012/0203306 A1* | 8/2012 | Sarvazyan | A61B 90/39 |
| | | | 607/61 |
| 2012/0220351 A1* | 8/2012 | Kerai | H04W 84/20 |
| | | | 455/574 |
| 2012/0275319 A1* | 11/2012 | Peiris | H04W 52/367 |
| | | | 370/339 |
| 2013/0018440 A1* | 1/2013 | Chow | A61N 1/37211 |
| | | | 607/61 |
| 2013/0030494 A1* | 1/2013 | Meredith | G16H 20/40 |
| | | | 607/9 |
| 2013/0094601 A1* | 4/2013 | Chang | H04B 7/10 |
| | | | 375/260 |
| 2013/0245981 A1* | 9/2013 | Estes | G01D 3/022 |
| | | | 702/87 |
| 2014/0064212 A1* | 3/2014 | Ko | H04L 1/0083 |
| | | | 370/329 |
| 2014/0113590 A1* | 4/2014 | Meylan | H04W 48/18 |
| | | | 455/411 |
| 2014/0323796 A1* | 10/2014 | Medvedev | A61M 60/538 |
| | | | 600/17 |
| 2014/0378057 A1* | 12/2014 | Ramon | H04L 9/3236 |
| | | | 455/41.2 |
| 2015/0065047 A1* | 3/2015 | Wu | H04W 4/80 |
| | | | 455/41.2 |
| 2015/0077244 A1* | 3/2015 | Lyman | G08B 25/016 |
| | | | 340/539.12 |
| 2015/0148868 A1* | 5/2015 | Shahandeh | A61N 1/37217 |
| | | | 607/60 |
| 2015/0341785 A1* | 11/2015 | Young | H04W 12/50 |
| | | | 607/60 |
| 2016/0279432 A1* | 9/2016 | Chappel | A61B 5/0022 |
| 2016/0328531 A1* | 11/2016 | DeCondo, Jr. | G16H 40/67 |
| 2017/0185284 A1* | 6/2017 | Bhavaraju | A61B 5/7435 |
| 2017/0222847 A1* | 8/2017 | Feher | H04L 27/0008 |
| 2018/0027077 A1* | 1/2018 | Melodia | H04B 11/00 |
| | | | 370/254 |
| 2018/0036547 A1* | 2/2018 | Reddy | A61N 1/3621 |
| 2019/0007817 A1* | 1/2019 | Liu | H04W 8/005 |
| 2019/0015669 A1* | 1/2019 | Muessig | A61B 5/0028 |
| 2019/0199562 A1* | 6/2019 | Feher | H04N 5/40 |
| 2019/0357283 A1* | 11/2019 | Liu | H04W 76/14 |
| 2020/0044844 A1* | 2/2020 | Sridhara | H04W 12/108 |
| 2020/0060558 A1* | 2/2020 | Aleksov | A61B 5/02141 |
| 2020/0069938 A1* | 3/2020 | Sinnott | A61N 1/362 |

* cited by examiner

IMPLANTABLE MEDICAL DEVICE AND METHOD FOR MANAGING A PHYSICAL LAYER UTILIZED DURING A WIRELESS CONNECTION

BACKGROUND

Embodiments of the present disclosure generally relate to techniques for managing wireless communication with implantable medical devices, and more particularly to the utilization of various physical layers during wireless communication.

An implantable medical device (IMD) is a medical device that is configured to be implanted within a patient anatomy and commonly employs one or more electrodes that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external device as well as control patient therapy. The IMD is completely enclosed within the human body. Thus, there is no means of direct interaction with an IMD, other than through wireless communication.

However, IMDs are typically built with non-replaceable batteries that limit options for communications solutions. Typically, the wireless communication is maintained utilizing a low range, low power communications platform during short periods of time. Existing communication solutions experience certain limitations regarding data transmission efficiency and rate. Currently, Bluetooth low energy (BLE) enabled IMDs use a static Bluetooth physical layer (PHY) and data rate during BLE communication irrespective of the type of transmission or how much data is being transferred. The standard settings are PHY=LE 1M with a data rate of 1 Mb/s. Using a common standard data rate for all transmissions throughout the life of an IMD is highly inefficient given that, for at least a portion of the time, the IMD is sending or receiving small amounts of data such as alerts and commands. Further, certain types of devices, such as miniature implantable medical devices, are more likely to send/receive alerts, commands or other smaller data sets. Miniature implantable medical devices have significant restrictions on battery demand which require that larger data transfers happen very infrequently. The foregoing are only a few examples of why different types of communications sessions are better suited to utilize different data rates and error correction schemes.

An ongoing demand exists to reduce power usage by IMDs. By limiting power usage, IMDs are able to last longer and be constructed with a smaller form factor. IMDs use a relatively large amount of power in connection with transmit and receive operations for BLE communications. Reducing the power usage for transmitting and receiving, however, will conflict with a separate demand for acceptable BLE communication distance. Creating and maintaining a strong BLE connection at an acceptable distance requires significant power consumption by the BLE transceiver.

Previously, it has been proposed to reduce the power demand by an IMD through defining an advertising schedule that uses different transmit power schemes. In accordance with at least one solution, methods and systems have been proposed that save power usage by defining an advertising schedule that includes a first transmit power setting when an external device (ED), communicating with an IMD, is in close proximity and a second transmit power setting when the ED is at a further distance. With the advancement of Bluetooth technology to the Bluetooth 5.0 standard, new opportunities are available for improving receiver sensitivity in order to conserve power consumption while at the same time optimizing communication distance.

BRIEF SUMMARY

In accordance with aspects herein, methods and devices are described to adaptively change transmission data rates and physical layers (PHY) to improve current consumption and/or RF performance. Using other PHYs can give advantages such as higher data rates or forward error correction (FEC) coding. Using lower data rates increases the ability of an implantable medical device and an external device to correctly receive each other's signal (improved receiver sensitivity) which effectively increases the communication range. Increasing receiver sensitivity means the corresponding transmit power levels can be decreased which saves power.

In accordance with new and unique aspects herein, methods and devices are described that use the lowest data rate for lower payload transmissions such as alerts and commands. This in turn creates a stronger communications connection so that either (1) the communication distance can be extended or (2) for the same communication distance, the transmit power can be reduced to save battery life. When data transfers or firmware updates are necessary, the BLE radios will switch back to the higher data rate momentarily until the transfers and updates are complete. Also, in addition to switching data rates, the methods and devices herein switch physical layers to provide additional benefits on top of the data rates.

In accordance with embodiments herein, an implantable medical device (IMD) is provided. The IMD includes a transceiver configured to communicate wirelessly, with an external device (ED), utilizing a protocol that utilizes multiple physical layers. The transceiver is configured to transmit information indicating that the transceiver is configured with first, second, and third physical layers (PHYs) for wireless communication. The IMD includes memory configured to store program instructions. The IMD includes one or more processors configured to execute instructions to obtain an instruction designating one of the first, second and third PHY to be utilized for at least one of transmission or reception, during a communication session, with the external device and manage the transceiver to utilize, during the communication session, the one of the first, second and third PHY as designated.

Optionally, the transceiver may be configured to transmit a communications packet to represent at least one of an advertisement packet, a scan request packet, or a scan response packet. The communications packet may include the information indicating that the transceiver is configured with the first, second and third PHYs. The transceiver may be configured to receive an ED communications packet from the external device. The ED communications packet may include the instruction designating the one of the first, second and third PHY. The one or more processors may be configured to at least one of 1) determine the type of communication or 2) determine a size of data set to be transferred between the ED and IMD. The one or more processors may be configured to generate the instruction designating the one of the first, second and third PHYs based on at least one of the type of communication or the size of the data set.

Optionally, the protocol may correspond to a Bluetooth protocol. The first, second and third PHY may correspond to LE 1M, LE 2M and LE Coded PHYs, respectively. The instruction may designate the LE 2M PHY when the type of communication corresponds to a large payload communication. The instruction may designate the LE Coded PHY when the type of communication corresponds to a small payload communication. The one or more processors may be configured to manage a receiver of the transceiver to utilize the first PHY in connection with receiving communications packets from the ED and may manage a transmitter of the transceiver to utilize the second PHY in connection with transmitting communications packets to the ED.

In accordance with embodiments herein, an external device (ED) configured to wirelessly communicate with an implantable medical device (IMD) utilizing a protocol that supports multiple physical layers (PHYs) is provided. The ED includes an external transceiver configured to wirelessly communicate with the IMD. The external transceiver is configured to receive a communications packet. The ED includes memory configured to store program instructions. The ED includes one or more processors that are configured, when implementing the program instructions, to analyze the communications packet for information indicating whether the IMD is configured with multiple physical layers (PHYs) for wireless communication, select one of the multiple PHYs based on at least one of a type of communication to occur, or a size of a data set to be transferred, during a communication session and transmit an instruction to the IMD to utilize the one of the multiple PHYs selected for at least one of transmission or reception during the communication session.

Optionally, the one or more processors may be further configured to receive, as the communications packet, an advertisement packet, and analyze a content of the advertisement packet for the information indicating where the IMD is configured with the multiple PHYs. The information analyzed from the communications packet may indicate whether the IMD is compatible with Bluetooth version 5.0 or higher. The one or more processors may be configured to determine the type of communication and select between first or second PHY based on the type of communication. The one or more processors may be configured to determine the size of the data set to be transferred and select between the second PHY or a third PHY based on the size of the data set to be transferred.

Optionally, following the select and transmit operations, the one or more processors may be configured to manage the external transceiver to establish a communication session with the IMD utilizing the one of the multiple PHYs. The one or more processors may be configured to initiate a communication session utilizing a first PHY from the multiple PHY and, to change, during the communication session, to a second PHY from the multiple PHY. The one or more processors may change to the second PHY based on a connection criteria that includes at least one of a data throughput requirement, a communication type, a battery indicator, a telemetry break condition, or link condition of the communications link between the IMD and ED.

In accordance with embodiments herein, a method for managing a wireless communication between an external device (ED) and an implantable medical device (IMD) utilizing a protocol that supports multiple physical layers (PHYs) is provided. The method selects, at one of the ED or IMD, one of multiple PHYs for wireless communication based on a connection criteria. The method transmits an instruction, to another of the ED or IMD, to utilize the one of the multiple PHYs selected for at least one of transmission or reception during the communication session.

Optionally, the method may receive, at the ED, a communications packet from the IMD and may analyze the communications packet for information indicating whether the IMD is configured with multiple physical layers (PHYs) for wireless communication. The ED may perform the selecting the one of the multiple PHYs and transmitting the instruction to the IMD. The method may collect and analyze the connection criteria. The connection criteria may include at least one of a data throughput requirement, a communication type, a battery indicator, a telemetry break condition, or link condition of a communications link between the IMD and ED. The method may determine at least one of 1) a type of communication or 2) a size of the data set to be transferred, and based thereon selecting the one of the multiple PHYs. The method may establish a communication session between the ED and the IMD utilizing the one of the multiple PHYs. The method pay initiate a communication session utilizing a first PHY from the multiple PHY and, changing, during the communication session, to a second PHY from the multiple PHY.

DETAILED DESCRIPTION

Figure 1:
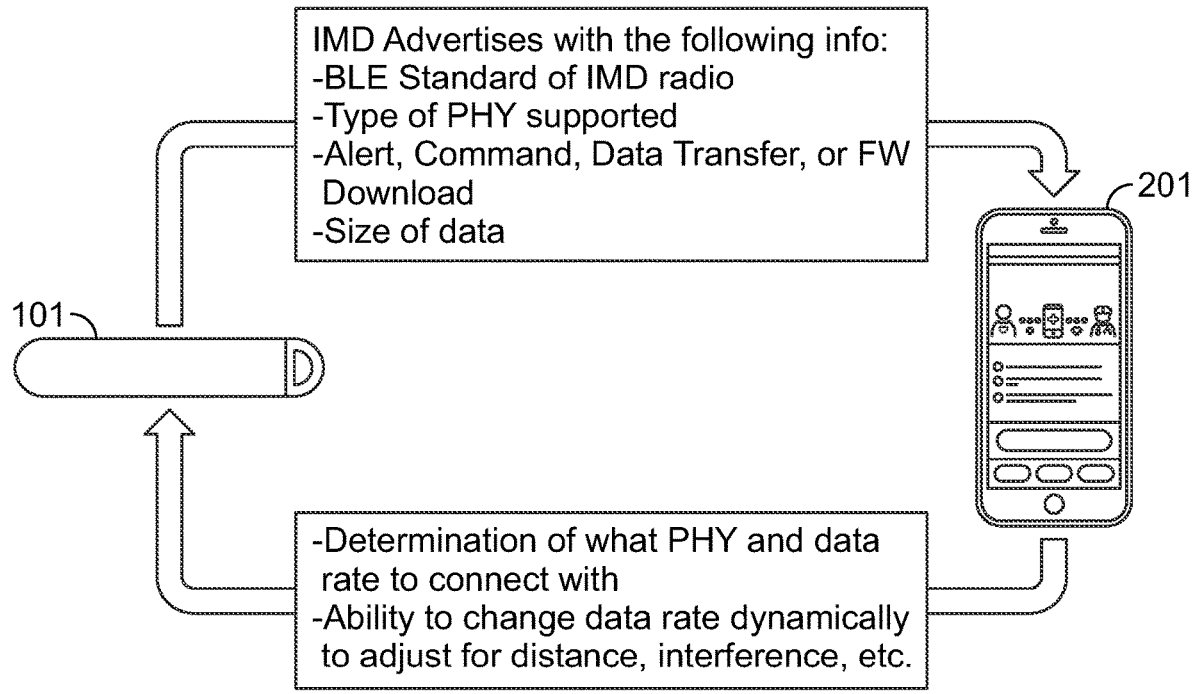
FIG. 1 illustrates a simplified block diagram of a system operated in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

The terms "small", "smaller", "large", and "larger", are used herein in connection with payload to refer to relative size to one another, and not to refer to a specific amount of data. For example, a first payload that is "smaller" as compared to a second payload, simply indicates that the first payload has less data than in the second payload.

The term "actual telemetry break", as used herein, refers to a condition in which a communications link has at least temporarily ended due to one or more of return errors and/or bad packets received by an IMD.

The term "potential telemetry break", as used herein, refers to a condition in which a communications link is maintained, but experiences a number of return errors and/or bad packets received by an IMD in excess of a threshold, thereby indicating a high likelihood that the communications link is about to end.

The term "telemetry break condition", as used herein, refers to a condition of a communications link with respect to an actual or potential telemetry break. A telemetry break condition represents one example of connection criteria.

The terms "low power" and "high power", as used herein, do not refer to absolute power levels, but instead referred to power levels relative to one another.

The term "connection criteria" refers to at least one of data throughput requirement, communication type, a battery indicator, a telemetry break condition or link condition of the communications link between the IMD and ED.

In accordance with new and unique aspects herein, methods and systems have been developed to take advantage of the availability of multiple physical layers (PHYs), such as the additions to the PHYs offered in the Bluetooth 5.0 and higher versions, in connection with improving transmission efficiency, limiting power usage and the like. The PHY represents the bottom layer of the protocol stack. Bluetooth 5.0 and later versions add two new PHY variance (LE 2M and LE coded) as compared to the single PHY variant offered in Bluetooth 4.2 and earlier versions (LE 1M). The LE 2M PHY allows the physical layer to operate at a rate of 2 million symbols per second (2 Ms/s), thereby enabling a higher data rate, as compared to the Bluetooth version 4.2 PHY of LE 1M (having a data rate of 1 million symbols per second). The terms "bits per second", "b/s", "symbols per second", and "s/s", are used interchangeably with one another throughout, although it is recognized that a symbol may not be limited to a single bit, but instead may be defined by a known number of bits. The LE 2M PHY doubles the symbol rate relative to the LE 1M PHY. The LE 1M PHY uses two level Gaussian frequency shift keying (GFSK) with a binary zero represented by a decrease in the carrier frequency by a given frequency deviation (185 kHz) and a binary one represented by increasing the carrier frequency by the same deviation (185 kHz). The LE 2M PHY uses two level GFSK with a binary zero represented by a decrease in the carrier frequency by a given frequency deviation (370 kHz) and a binary one represented by increasing the carrier frequency by the same deviation (370 kHz).

The LE coded PHY allows the communication range to be greatly increased, such as potentially quadrupled, as compared to the range afforded by the LE 1M PHY in accordance with the Bluetooth 4.2 version (all other factors and the environment being equal). The increased range of the LE coded PHY is achieved without increasing the transmission power required, through the use of forward error correction (FEC). However, the added error correction capability afforded in the LE coded PHY sacrifices data rate. More specifically, the LE 1M PHY and LE 2M PHY utilize error detection, such as a cyclic redundancy check (CRC), in which a CRC value is calculated for data packets by the transmitter and appended to the packet. The receiver recalculates the CRC and compares the recalculated value with the value appended to the packet. When the values are not the same, an error is declared. When an error is detected, the receiver requests or "hints" (e.g., by failing to acknowledge receipt of a packet at the link layer) that the transmitter resend the data packet. When a transceiver receives a request for data to be resent, or when a transceiver does not receive an acknowledgment, the transceiver resends the data packet.

The LE coded PHY adds advanced error correction that enables the receiver to not need the data to be retransmitted, but instead allows the receiving device to perform error "correction" (not simply error "detection" as in Bluetooth version 4.2). The forward error correction adds additional redundant bits to transmitted packets, where the redundant bits are intended to support application of the FEC algorithm and to determine the correct value for received bits. By way of example, the FEC encoding may utilize a convolution encoder which generates S-bits for each input bit using a predetermined generator polynomial. Different coding schemes may be utilized, such as a 2-bit (S=2) or an 8-bit (S=8). In a 2-bit encoding scheme, the convolution encoder outputs 2 bits for each single input bit. In a 8-bit encoding scheme, the convolution encoder outputs 8-bits for each single input bit. A pattern mapper converts each bit from the convolution FEC encoder into P symbols where the value of P depends on the coding scheme. When a 2-bit coding scheme is used P=1, when an 8-bit coding scheme is utilized, P=4. The different coding schemes affect transmission range, with the LE Coded 2S scheme PHY having a range that is approximately double the range of the LE 1M PHY, while the range corresponding to the LE coded 8S scheme PHY is approximately four times greater than the range afforded by the LE 1M PHY. However, the data rate associated with the LE coded 8S scheme drops to 125 kb per second (125 Ks/s), and the data rate associated with LE coded 2S scheme drops to 500 kb per second (500 Ks/s), as compared to the 1 Mb per second (1 Ms/s) data rate of the LE 1M PHY.

In accordance with new and unique aspects herein, methods and systems are described that actively switch to different physical layers (PHY) and corresponding data rates depending upon a type of communication and/or an amount of data to be transferred during the communication session. Embodiments herein seek to maximize the nature of the three different physical layers: LE 1M, LE 2M, and LE Coded. LE 1M is the most common PHY and is compatible with all Bluetooth transceivers. LE 1M can only support the 1 Mb/s data rate and does not support any error corrections. LE 2M can support heavier data transfer loads of 2 Mb/s. LE Coded can support lower data rates such as 125 Kb/s and 500 Kb/s. LE Coded can also use forward error correction to recover erroneous data packets to improve the fidelity of the signal reception. In order to use LE 2M or LE Coded PHYs, both an IMD and an external device must use transceivers that are compliant to the Bluetooth 5.0 standard.

Table 1 below shows a comparison of the effects upon performance when using different PHY and data rates. Performance may be defined in various manners, such as based on bit error rate, signal to noise ratio, dropped connections, number of data packets that are not properly received, and the like. At the lower data rates, when using the LE Coded PHY, significant improvements can be seen regarding communication distance and current savings while maintaining a constant performance. The LE 1M PHY serves as a baseline as it is the current setting for conventional IMDs. Using a 2 Mb/s data rate will allow larger amounts of data to be transferred faster at the cost of shorter communication range and more power consumption. The lower data rates provide significant improvements in communication distance and power consumption.

TABLE 1

TABLE OF PERFORMANCE VS. DATA RATE AND PHY

| PHY | Data Rate | Loss/Gain (dB) | Distance | Current Consumption |
|---|---|---|---|---|
| LE 2M | 2 Mb/s | −3.1 | 0.7 × D | −29% |
| LE 1M | 1 Mb/s | 0 | D | 0% |
| LE Coded 2S | 500 Kb/s | +4.4 | 1.66 × D | 29% |
| LE Coded 8S | 125 Kb/s | +7.0 | 2.24 × D | 40% |

Table 1 illustrates differences in loss/gain (in dB), distance and current consumption in connection with each PHY and data rate relative to reference levels associated with the LE 1M PHY. The loss/gain column represents an amount that the transceiver will need to increase or decrease the gain, relative to a reference level, to afford a same performance level as the reference LE 1M PHY. As shown in Table 1, in order to maintain a same level of performance as the LE 1M PHY, when the PHY is switched to the LE 2M PHY, (e.g., with all other factors remaining equal such as distance, interference, overall environment), the transceiver gain needs to be increased by 3.1 dB. In other words, when an IMD switches from the LE 1M PHY to the LE 2M PHY, the IMD would need to increase the transmit/receive gain by 3.1 dB to maintain a common communication link quality at a given distance D relative to the transmit/receive gain that the transceiver was utilizing when communicating over the LE 1M PHY. The increase of 3.1 dB of gain causes an increase in current consumption by the IMD of approximately 29% as compared to the current consumption of the IMD when utilizing the LE 1M PHY.

Conversely, when switching from the LE 1M PHY to the LE Coded 2S or LE Coded 8S PHY, if all other factors are maintained constant, the transceiver gain could be decreased by 4.4 dB and 7.0 dB, respectively, (below the gain setting utilized by the LE 1M PHY) to maintain a common communication link quality at a given distance D relative to the transmit/receive gain when communicating utilizing the LE 1M PHY. The decreases of 4.4 dB and 7.0 dB of gain results in lower current consumption by the IMD (when utilizing the LE Coded 2S or LE Coded 8S PHY) of approximately 29% and 40%, respectively, as compared to the current consumption of the IMD when utilizing the LE 1M PHY.

Alternatively, if the IMD maintains the transmit/receive gain/sensitivity constant when switching from the LE 1M to the LE 2M PHY, the IMD will exhibit a same performance, when utilizing the LE 2M PHY at a shorter communications distance, namely at distance of 0.7D relative to the reference distance (D) associated with the LE 1M PHY. Conversely, when switching from the LE 1M PHY to the LE Coded 2S or LE Coded 8S PHY, if all other factors are maintained constant, when the IMD utilizes the LE Coded 2S or LE Coded 8S PHY, the IMD will exhibit a same performance, as when using the LE 1M PHY, at greater communications distances of 1.66D and 2.44D, respectively.

FIG. 1 illustrates a simplified block diagram of a system operated in accordance with embodiments herein. The system includes one or more IMD 101 and one or more external device (ED) 201 (e.g., table computer, smart phone, smart watch, laptop, and/or the like) that are configured to communicate with one another wirelessly over a communications link.

The IMD 101 is implanted within a patient (e.g., proximate to and/or within a heart, proximate to the spinal cord).

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may deliver some type of therapy/treatment, provide mechanical circulatory support and/or merely monitor one or more physiologic characteristics of interest (e.g., PAP, CA signals, impedance, heart sounds).

Additionally or alternatively, the IMD may be any of the implantable devices described in U.S. application Ser. No. 16/930,791, titled "METHODS, DEVICES AND SYSTEMS FOR HOLISTIC INTEGRATED HEALTHCARE PATIENT MANAGEMENT", filed Jul. 16, 2020, which is incorporated by reference in its entirety. As non-limiting examples, the IMD may be a body generated analyte or BGA test device which shall mean any and all equipment, devices, disposable products utilized to collect and analyze a BGA. The terms "body generated analyte" and "BGA" shall have the meaning defines in the U.S. application Ser. No. 16/930,791. The BGA test device may implement one or more of the methods, devices and systems described in the following publications, all of which are incorporated herein by reference in their entireties: U.S. Patent Publication Number 2011/0256024, entitled "MODULAR ANALYTE MONITORING DEVICE", published Oct. 20, 2011; U.S. Patent Publication Number 2010/0198142, entitled "MULTIFUNCTION ANALYTE TEST DEVICE AND METHODS THEREFORE", published Aug. 5, 2010; U.S. Patent Publication Number 2011/0160544, entitled "SYSTEM AND METHOD FOR ANALYSIS OF MEDICAL DATA TO ENCOURAGE HEALTHCARE MANAGEMENT", published Jun. 30, 2011; U.S. Pat. No. 5,294,404, entitled "REAGENT PACK FOR IMMUNOASSAYS" issued Mar. 15, 1994; U.S. Pat. No. 5,063,081, entitled "METHOD OF MANUFACTURING A PLURALITY OF UNIFORM MICROFABRICATED SENSING DEVICES HAVING AN IMMOBILIZED LIGAND RECEPTOR" issued Nov. 5, 1991; U.S. Pat. No. 7,419,821, entitled "APPARATUS AND METHODS FOR ANALYTE MEASUREMENT AND IMMUNOASSAY" issued Sep. 2, 2008; U.S. Patent Publication Number 2004/0018577, entitled "MULTIPLE HYBRID IMMUNOASSAYS" published Jan. 29, 2004; U.S. Pat. No. 7,682,833, entitled "IMMUNOASSAY DEVICE WITH IMPROVED SAMPLE CLOSURE" issued Mar. 23, 2010; U.S. Pat. No. 7,723,099, entitled "IMMUNOASSAY DEVICE WITH IMMUNO-REFERENCE ELECTRODE" issued May 25, 2010; and Baj-Rossi et al. "FABRICATION AND PACKAGING OF A FULLY IMPLANTABLE BIOSENSOR ARRAY", (2013) IEEE, pages 166-169, all of which are incorporated by reference in their entireties.

The determination of which physical layer and data rate to be utilized may be initiated when the transceiver of the IMD 101 sends out advertisement packets and/or at any point during a communications session. The advertisement packets may include information such as the BLE Standard (e.g., Bluetooth 4.0, 4.2, 5.0) supported by the IMD, compatible PHY types (LE 1M, LE 2M, LE Coded), a type of communication to occur (e.g., alert, command, software update, data transfer, etc.), and size of the data to be transferred. When the external device 201 (e.g., programmer, bedside monitor, smartphone, etc.) receives the advertisement packet, the external device 201 will determine based on the encoded information how best to connect to the IMD 101. Once the external device 201 knows the IMD transceiver capabilities, the external device 201 can control the transceiver parameters both at the initial connection state and throughout the communication session in order to provide a desired (e.g., optimal) RF performance. Once a communication session is initiated, the ED 201 is afforded the ability to change the PHY and data rate dynamically to adjust for circumstances such as changes in distance between the IMD 101 and ED 201, changes in orientation of the patient (and IMD 101) relative to the ED 201, changes in interference and the like.

Figure 2A:
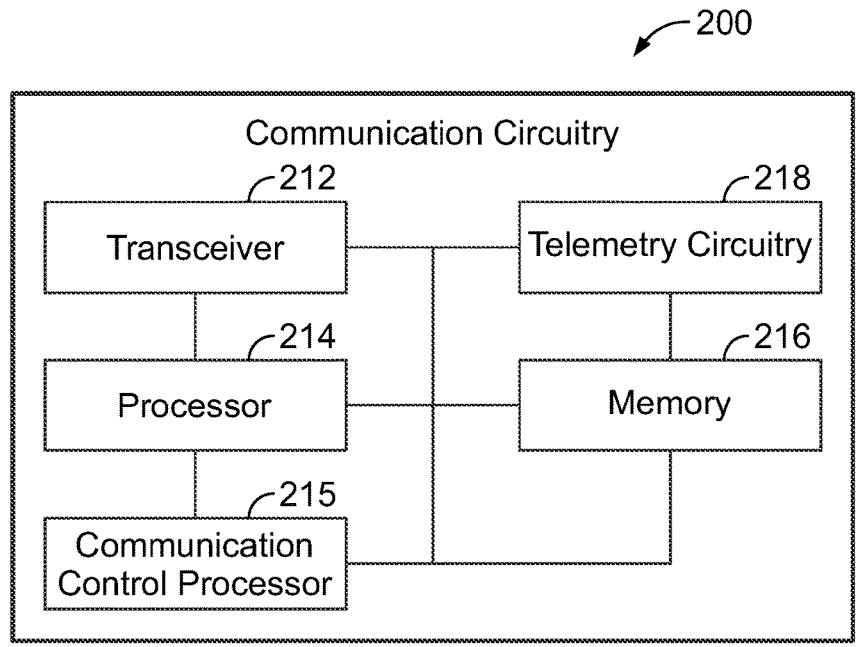
FIG. 2A illustrates a block diagram of communication circuitry utilized in accordance with an embodiments herein.

FIG. 2A illustrates a block diagram of communication circuitry 200 utilized in accordance with an embodiments herein. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The communication circuitry 200 is within an IMD and optionally within one or more external device. The communication circuitry 200 is configured to establish and maintain the communication link between the IMD 101 and external devices. In one example, the communication circuitry 200 may be configured to handle and/or manage the bi-directional communication link between the IMD 101 and the ED 201. In one example, the communication circuitry 200 is an RF circuit. In another example, the communication circuitry 200 includes a transponder that transmits signals and a receiver that receives signals. In yet another example, the communication circuitry 200 includes a transceiver 212 (TX/RX) that both transmits signals and receives signals. Specifically, a transceiver includes both a transponder and a receiver. As explained herein, the communication circuitry 200 transmits, among other things, advertisement notices, connection requests, connection responses, scan requests, scan responses, data packets and the like. The transceiver 212 is tuned to communicate with external devices, including the ED 201 over one or more frequency bands and in accordance with a corresponding protocol. The transceiver 212 may include one or more transmitters/transponders, receivers, and/or transceivers. Optionally, the communication circuitry 200 may be electrically coupled to an antenna (not shown). For example, an antenna may be provided within a header of an IMD as one example. As another example, electrodes on or coupled to the IMD may be utilized to convey the wireless communication signals. The communication circuitry 200 also scans for connection request data packets from external devices. In one example the external device is the ED 201 of FIG. 1.

The communication circuitry 200 also includes one or more processors 214 including a communication control processor 215, a local memory 216, and telemetry circuitry 218, all of which may be implemented on a common circuit board, within a common subsystem or within a common integrated circuit. Specifically, the communication circuitry 200 is in communication with other circuits, components, and modules of the IMD 101 including controller circuit, and local memory 216. The communication control processor 215 may support one or more wireless communication protocols while communicating with an external device such as the ED 201, such as Bluetooth low energy, Bluetooth, Medical Implant Communication Service (MICS), and/or the like.

The memory 216 stores instructions implemented by the communication control processor 215. Protocol firmware may be stored in memory 216, which is accessed by the communication control processor 215. The protocol firmware provides the wireless protocol syntax for the communication control processor 215 to assemble data packets, advertisement notices, connection request data packets, connection responses, establish communication links, such as communication, and/or partition data received from an external device, such as ED 201.

The telemetry circuitry 218 in one example monitors the quality of the telemetry or communications link. Alternatively, the telemetry software is stored in the memory that provides instructions that are followed by the communication control processor or one or more of the processors 214 related to the communication circuitry 200. The telemetry circuitry 218 in one example determines when the link, and/or how often the link drops causing interruptions in communications being passed through the communications link. In another example the telemetry circuitry 218 determines the number of return errors received, number of bad packets received, or the like. Optionally, the telemetry circuitry 218 tracks the signal to noise ratio (RSSI) of the communication link. When the communication link is down or not working the telemetry circuitry 218 verifies the power setting of the telemetry link and increases the power setting when a break in the link occurs, or when a link is unable to be established. In this manner, the telemetry circuitry 218 facilitates re-establishment of the link to assist in completing communication sessions. Thus, the telemetry circuitry 218 not only makes determinations regarding when communication breaks occurs including timing to reestablish the link and the like, but additionally, the quality of the telemetry link is determined through various methods including RSSI. The telemetry circuitry 218 also actively corrects any breaks or poor quality communications by increasing power to establish and maintain the link.

Figure 2B:
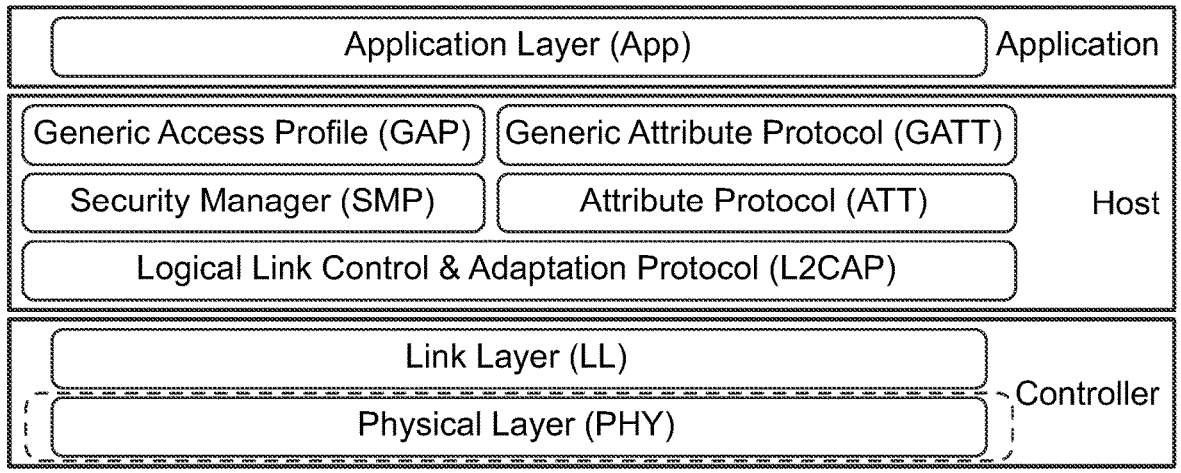
FIG. 2B illustrates a full protocol stack structure of a Bluetooth protocol in accordance with an embodiments herein.

FIG. 2B illustrates a full protocol stack structure of a Bluetooth protocol. The top layer corresponds to various applications that interact with and utilize Bluetooth wireless communication. The host maintains various information, such as the generic access profile (GAP), generic attribute protocol (GATT), secure manager (SMP), attribute protocol (ATT), and logical Link control and adaptation protocol (L2CAP). The controller implements, among other things, the link layer (LL) and the physical layer (PHY).

Returning to FIG. 2A, the communications circuitry 200 is configured to implement the Bluetooth low energy protocol of FIG. 2B, including the multiple physical layers discussed herein. As explained herein, the communications circuitry 200 is configured to support bidirectional communications utilizing a selected one of the LE 1M, LE 2M, LE Coded physical layers (including the LE Coded 2S and LE Coded 8S). Optionally, during a communications session, the communications circuitry 200 may transmit utilizing a first PHY and receive utilizing a second PHY. For example, during a communications session in which the IMD is downloading a new firmware version, the IMD may receive data utilizing the LE 2M PHY, while utilizing one of the LE Coded PHY to transmit to the ED. As another example, during a communication session in which the IMD is uploading stored EGM signals, the IMD may utilize the LE 2M PHY to transmit the EGM signals to the ED, but utilize one of the LE Coded PHY to receive commands from the ED.

As explained herein, the communications circuitry 200 is configured to communicate wirelessly, with an external device (ED), utilizing a protocol that utilizes multiple physical layers. The communications circuitry 200 is configured to transmit information indicating that the transceiver is configured with first, second and third physical layers (PHYs) for wireless communication. The IMD further comprises memory 216 configured to store program instructions and one or more processors 214 configured to execute instructions to: obtain an instruction designating one of the first, second and third PHY to be utilized for at least one of transmission or reception, during a communication session, with the external device; and manage the transceiver 212 to utilize, during the communication session, the one of the first, second and third PHY as designated.

For example, the transceiver 212 is configured to transmit a communications packet represents at least one of an advertisement packet, a scan request packet or a scan response packet, the communications packet including the information indicating that the transceiver is configured with the first, second and third PHYs. Additionally or alternatively, the transceiver 212 is configured to receive an ED communications packet from the external device, the ED communications packet including the instruction designating the one of the first, second and third PHY. Additionally or alternatively, the one or more processors 214 are configured to at least one of 1) determine the type of communication or 2) determine a size of data set (also referred to as a data throughput requirement) to be transferred between the ED and IMD, the one or more processors 214 configured to generate the instruction designating the one of the first, second and third PHYs based on at least one of the type of communication or the size of the data set.

In accordance with embodiments herein, when the protocol corresponds to a Bluetooth protocol, the first, second and third PHY corresponding to LE 1M, LE 2M and LE Coded PHYs, respectively, and the instruction designates the LE 2M PHY when the type of communication corresponds to a large payload communication. The instruction designates the LE Coded PHY when the type of communication corresponds to a small payload communication. The one or more processors are configured to manage a receiver of the transceiver to utilize the first PHY in connection with receiving communications packets from the ED and to manage a transmitter of the transceiver to utilize the second PHY in connection with transmitting communications packets to the ED.

In accordance with embodiments herein, the ED is also configured to wirelessly communicate with the IMD utilizing a protocol that supports multiple physical layers (PHYs). The ED comprises an external transceiver configured to wirelessly communicate with the IMD; the external transceiver configured to receive a communications packet; memory configured to store program instructions; and one or more processors that are configured, when implementing the program instructions, to: analyze the communications packet for information indicating whether the IMD is configured with multiple physical layers (PHYs) for wireless communication; select one of the multiple PHYs based on at least one of a type of communication to occur, or a size of a data set to be transferred, during the communication session; and transmit an instruction to the IMD to utilize the one of the multiple PHYs selected for at least one of transmission or reception during the communication session.

Additionally or alternatively, the one or more processors are further configured to receive, as the communications packet, an advertisement packet, and analyze a content of the advertisement packet for the information indicating where the IMD is configured with the multiple PHYs. Additionally or alternatively, the information analyzed from the communications packet indicates whether the IMD is compatible with Bluetooth version 5.0 or higher. Additionally or alternatively, the one or more processors are configured to determine the type of communication and select between first or second PHY based on the type of communication. Additionally or alternatively, the one or more processors are configured to determine the size of the data set to be transferred and select between the second PHY or a third PHY based on the size of the data set to be transferred. Additionally or alternatively, following the select and transmit operations, the one or more processors are configured to manage the device transceiver to establish a communication session with the IMD utilizing the one of the multiple PHYs.

Figure 3:
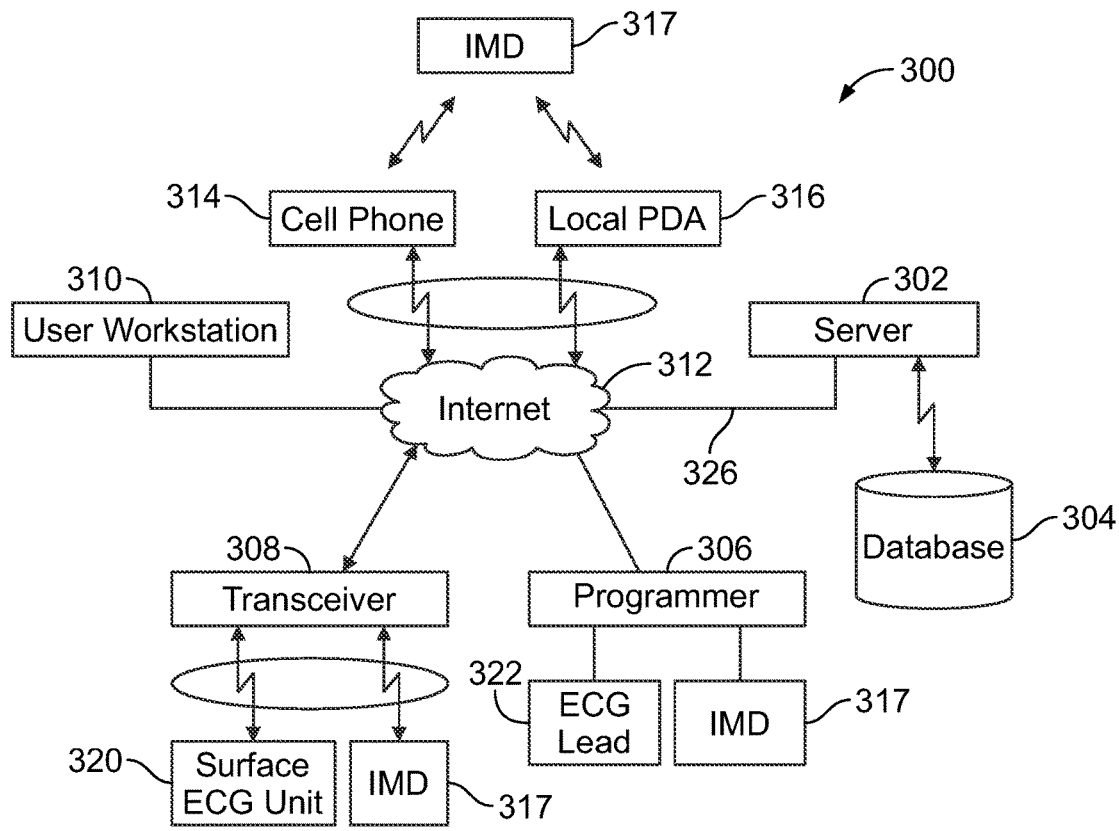
FIG. 3 illustrates a distributed processing system in accordance with one embodiment.

FIG. 3 illustrates a distributed processing system 300 in accordance with one embodiment. In one example, the distributed processing system 300 includes and implements the communication circuitry 200 as provided in FIG. 2A in one or more of the devices shown in FIG. 3. The distributed processing system 300 includes a server 302 connected to a database 304, a programmer 306, a local RF transceiver 308 and a user workstation 310 electrically connected to a communication system 312. Any of the processor-based components in FIG. 3 (e.g., workstation 310, cell phone 314, PDA 316, server 302, programmer 306, IMD 101) may communicate with an IMD 317 that in one example is IMD 101 of FIG. 1. In one example, the local RF transceiver 308 is the transceiver of 212 of FIG. 2A. The various components illustrated in FIG. 3 are configured to communicate over a common wireless protocol, such as the Bluetooth low energy protocol. The components may implement various versions of the BLE protocol. For example, a subset of the IMDs 317 may implement a version 4.0 or lower version of the BLE protocol (e.g., having only the LE 1M PHY), while another subset of the IMD 317 may implement a version 5.0 or higher version of the BLE protocol (e.g., having multiple PHYs). The cell phone 314 and programmer 306 may include transceivers that support multiple PHYs (e.g., LE 1M, LE2M, LE coded), while the local PDA 316 only supports the LE 1M PHY.

Various components within the system 300 may determine which PHY to utilize during communication, including but not limited to, the IMD 317, cell phone 314, local PDA 316, transceiver 308, programmer 306 and server 302. For example, the programmer 306 and/or cell phone 314 may initially determine which physical layer to utilize during a communication session. Additionally or alternatively, an IMD 317, with which the cell phone 314 and/or programmer 306 communicate, may make the initial determination of the physical layer. Additionally or alternatively, the IMD 317 may determine that the initial physical layer designator for communication is not affording a sufficient level of performance or signal quality and instruct the cell phone 314, programmer 306 or other external device to switch to a more reliable physical layer (e.g., switching from the LE 2M layer to the LE 1M or LE Coded layer).

The communication system 312 may be the internet, a voice over IP (VoIP) gateway, a local plain old telephone service (POTS) such as a public switched telephone network (PSTN), a cellular phone based network, and the like. Alternatively, the communication system 312 may be a local area network (LAN), a campus area network (CAN), a metropolitan area network (MAN), or a wide area network (WAN). The communication system 312 serves to provide a network that facilitates the transfer/receipt of information such as cardiac signal waveforms, ventricular and atrial heart rates.

The server 302 is a computer system that provides services to other computing systems over a computer network. The server 302 interfaces with the communication system 312 to transfer information between the programmer 306, the local RF transceiver 308, the user workstation 310 as well as a cell phone 314, a personal data assistant (PDA) 316, and IMD 317 to the database 304 for storage/retrieval of records of information. On the other hand, the server 302 may upload raw cardiac signals from an implanted lead 322, surface ECG unit 320 or the IMD 317 via the local RF transceiver 308 or the programmer 306.

The database 304 stores information such as cardiac signal waveforms, ventricular and atrial heart rates, thresholds, and the like, for a single or multiple patients. The information is downloaded into the database 304 via the server 302 or, alternatively, the information is uploaded to the server from the database 304. The programmer 306 is similar to an external device or instrument and may reside in a patient's home, a hospital, or a physician's office. The programmer 306 interfaces with the lead 322 and the IMD 317. The programmer 306 may wirelessly communicate with the IMD 317 and utilize protocols, such as Bluetooth, GSM, infrared wireless LANs, HIPERLAN, 3G, satellite, inductive as well as circuit and packet data protocols, and the like. Alternatively, a hard-wired connection may be used to connect the programmer 306 to the IMD 317. The programmer 306 is able to acquire cardiac signals from the surface of a person (e.g., ECGs), intra-cardiac electrogram (e.g., IEGM) signals from the IMD 317, and/or cardiac signal waveforms, ventricular and atrial heart rates, and detection thresholds from the IMD 317. The programmer 306 interfaces with the communication system 312, either via the internet or via POTS, to upload the information acquired from the surface ECG unit 320, the lead 322 or the IMD 317 to the server 302.

The local RF transceiver 308 interfaces with the communication system 312 to transmit and receive telemetry data and information being transmitted to and from the RF transceiver 308. In one example the communication system monitors the communication link and records telemetry breaks, length of breaks, number of breaks in a given interval, time to reestablish a signal, signal to noise ratio, and the like. In this manner the communication system 312 provides with a user the quality and/or strength of a communication signal and amount or strength of local interference. In addition, the communication system 312 (e.g., server 302, cell phone 314, work station 310, programmer 306) may, based on the monitored communication quality, increase or decrease the power of a signal being transmitted. In one example, the communication system 312 monitors both advertising channels and connection channels, thus providing advertising data packets through and communicating through the advertising channels with external devices. Similarly, the communication system 312 is able to provide a communication pathway through a connection channel.

The user workstation 310 may interface with the communication system 312 to download cardiac signal waveforms, ventricular and atrial heart rates, and detection thresholds via the server 302 from the database 304. Alternatively, the user workstation 310 may download raw data from the surface ECG units 320, lead 322 or IMD 317 via either the programmer 306 or the local RF transceiver 308 or cell phone 314 or PDA 316. Once the user workstation 310 has downloaded the cardiac signal waveforms, ventricular and atrial heart rates, or detection thresholds, the user workstation 310 may process the information in accordance with one or more of the operations described above. The user workstation 310 may download the information and notifications to the cell phone 314, the PDA 316, the local RF transceiver 308, the programmer 306, or to the server 302 to be stored on the database 304.

Process for Managing a Physical Layer Utilized for Communication

Figure 4:
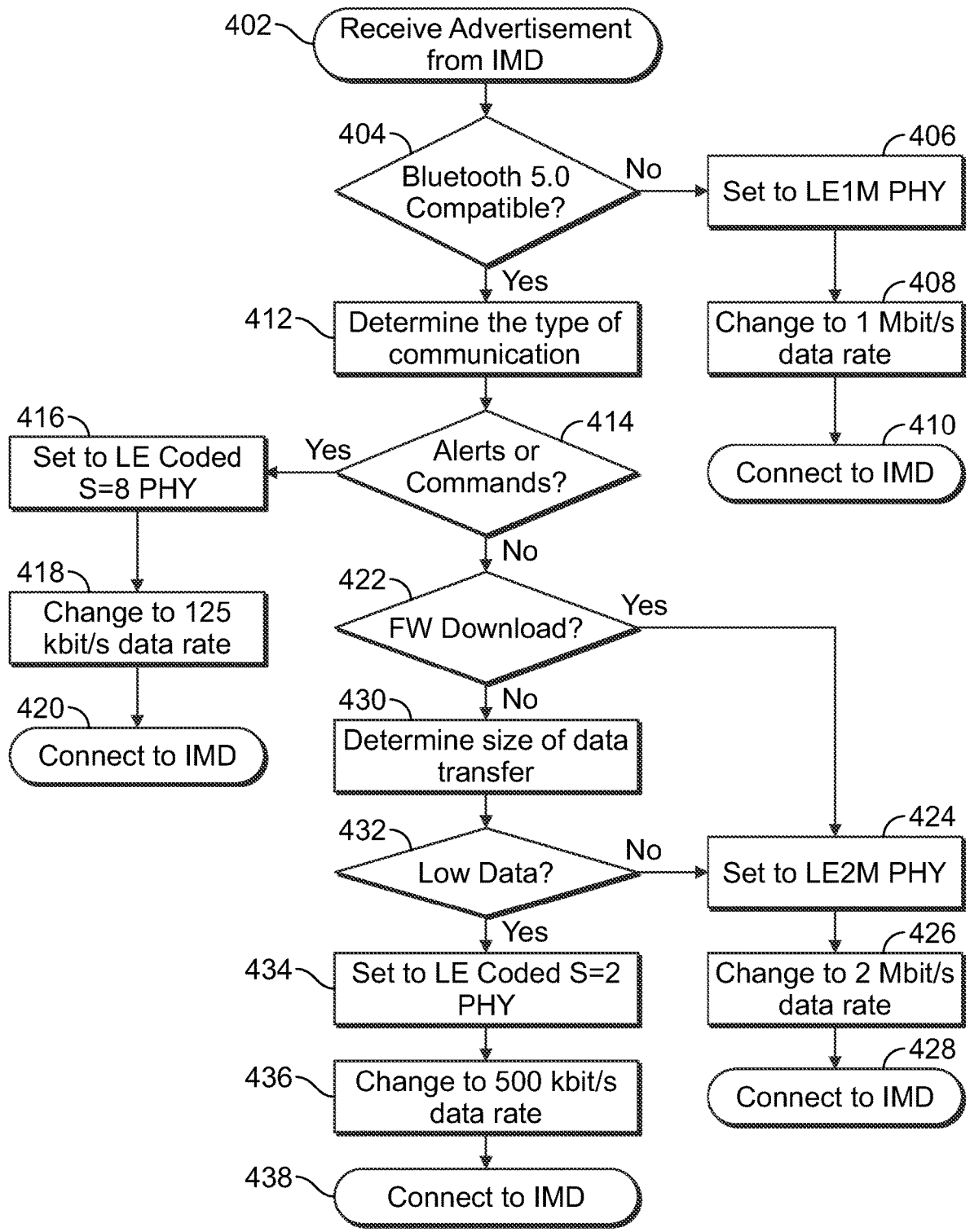
FIG. 4 illustrates a flow block diagram of a method for managing physical layer usage for communication between an external device and an implantable medical device in accordance with one embodiment.

FIG. 4 illustrates a flow block diagram of a method for managing physical layer usage for communication between an external device and an implantable medical device. The method may be implemented by hardware components, software components, and/or a combination of hardware components and software components working together to implement the method. The following description will be provided in the context of an external device acting as a host by receiving an advertisement and making the various determinations to select the PHY to be utilized. Although, it is understood that in certain instances, the IMD may serve as the host, and in other instances, a remote server may serve as the host when directly or indirectly communicating with an IMD.

At 402, one or more processors of the host (e.g., external device) receive a communications packet transmitted by the slave (e.g., IMD). For example, the communications packet may represent at least one of an advertisement packet, a connect request packet, a connect response packet, a scan request packet, a scan response packet, and the like. The communications packet includes information indicating whether the transceiver of the IMD is configured with the first, second and third PHYs. Additionally or alternatively, the transceiver is configured to receive an ED communications packet from the external device, the ED communications packet including the instruction designating the one of the first, second and third PHY. Additionally or alternatively, the one or more processors are configured to at least one of 1) determine the type of communication or 2) determine a size of data set (data throughput requirement) to be transferred between the ED and IMD, the one or more processors configured to generate the instruction designating the one of the first, second and third PHY's based on at least one of the type of communication or the size of the data set.

At 404, the one or more processors of the host analyze the advertisement notice to determine certain information about the IMD. Among other things, the host/master determines communications capability information about the IMD, such as which Bluetooth standard is supported by the IMD (e.g., Bluetooth 4.0, 4.2, 5.0), compatible PHY types supported by the IMD (e.g., LE 1M, LE2M, LE coded) and the like. When the IMD is determined to support Bluetooth 5.0 or above versions and/or determined to be compatible with PHY types of LE 2M and LE coded, flow moves to 412. Otherwise, flow moves to 406.

At 406, the one or more processors of the host set the PHY to be utilized during the transmit and receive operations to a first PHY that may represent the only PHY type supported by the IMD (e.g., the LE 1M PHY). At 408, the transceiver of the host changes to the first PHY level and the corresponding data rate. In the present example, the transceiver switches to maintain a data rate of 1 Mb/s.

At 410, the host and the slave exchange additional information to establish a communications session. The operations at 406-410 may be implemented utilizing the PHY Update Procedure, as described in Section 5.1.10 the Bluetooth Specification Version 5.0, volume 6, part B. The "capitalize" field names described herein shall have the meanings set forth in the Bluetooth Specification version 5.0, volume 6. The Bluetooth specification Version 5.0, volume 6 is expressly incorporated herein by reference in its entirety. The PHY update procedure may be initiated either upon request by the host or autonomously by the link layer of the slave. Either the master or slave (e.g., external device or IMD) may initiate the PHY update procedure at any time after entering the connection state. The link layer PHY preferences may change during a connection or between connections and therefore, are not necessarily cached by peer devices. When the PHY update procedure is initiated by the host/master (e.g., external device), the host/master sends an LL_PHY_REQ PDU (link layer PHY request protocol data unit). The slave/IMD responds with an LL_PHY_UPDATE_IND PDU (LL PHY update indication PDU).

Alternatively, when the PHY update procedure is initiated by the slave/IMD, the IMD sends an LL_PHY_REQ PDU, in response to which the master/ED responds with an LL_PHY_UPDATE_IND PDU. The TX_PHYS (transmit physical later) and RX_PHYS (receive PHY) fields of the LL_PHY_REQ and LL_PHY_RSP PDUs shall be used to indicate the PHYs that the sending link layer prefers to use. If the sender wants a symmetric connection (e.g., one where the two PHYs are the same), the sender should make both fields the same, only specifying a single PHY. The M_TO_S_PHY (Master to slave physical layer) and the S_TO_M_PHY (slave to master physical layer) fields of the LL_PHY_UPDATE_IND PDU shall indicate the PHYs that should be used after the incident. If the master initiates the PHY update procedure, the master shall determine the PHY to use in each direction based on the contents of the LL_PHY_REQ and LL_PHY_RSP protocol data units (PDUs) using the following rules: 1) the M_TO_S_PHY field of the LL_PHY_UPDATE_IND PDU shall be determined from the master's TX_PHYS field and the slave's RX_PHYS field; 2) the S_TO_M_PHY field of the LL_PHY_UPDATE_IND PDU shall be determined from the master's RX_PHYS field and the slave's TX_PHYS field. In each of the foregoing cases, the following rules apply: 1) if, for at least one PHY, the corresponding bit is set to 1 in both the TX_PHYS and RX_PHYS fields, the master shall select any one of those PHYs for that direction; 2) if there is no PHY for which the corresponding bit is set to 1 in both the TX_PHYS and RX_PHYS fields, the master shall not change the PHY for that direction.

If the slave initiates the PHY update procedure, the master shall determine the PHY to use in each direction based on the contents of the LL_PHY_REQ PDU sent by the slave using the following rules: 1) the M_TOS_PHY field of the LL_PHY_UPDATE_IND PDU shall be determined from the RX_PHYS field of the slave's PDU; 2) the S_TO_M_PHY field of the LL_PHY_UPDATE_IND PDU shall be determined from the TX_PHYS field of the slave's PDU. In each of the foregoing cases the following rules apply: 1) if, for at least one PHY, the PHY is one that the master prefers to use and the corresponding bit is set to 1 in the relevant field of the slave's PDU, the master shall select any one of those PHYs for that direction; 2) if there is no PHY which the master prefers to use and for which the corresponding bit is set to 1 in the relevant field of the slave's PDU, the master shall not change the PHY for that direction.

The following discussion shall apply irrespective of which device initiated the PHY update procedure. Irrespective of the above rules, the master may leave both directions unchanged. If the slave specified a single PHY in both the TX_PHYS and RX_PHYS fields and both fields are the same, the master shall either select the PHY specified by the slave for both directions or shall leave both directions unchanged. Both devices shall use the new PHYs starting at the instant. If a master or slave sends an LL_PHY_REQ PDU to a device that does not understand that PDU, then the receiving device shall send an LL_UNKNOWN_RSP PDU in response. The procedure has completed when: 1) an LL_UNKNOWN_RSP or LL_REJECT_EXT_IND PDU has been sent or received; 2) an LL_PHY_UPDATE_IND PDU indicating that neither PHY will change has been sent or received; or 3) the master sends an LL_PHY_UPDATE_IND PDU indicating that at least one PHY will change and the instant has been reached. In this case, the procedure response timeout shall be stopped on the master when it sends that PDU and on the slave when it receives that PDU. The controller shall notify the host of the PHYs now in effect when the PHY Update Procedure completes if either it has resulted in a change of one or both PHYs or if the procedure was initiated by a request from the Host. Otherwise, it shall not notify the host that the procedure took place.

Returning to 404, when flow moves to 412, the one or more processors of the host determine the type of communication to occur. Nonlimiting examples of communication types may include alert communications, command communications, software updates, data transfers and the like. Alert and command type communications include relatively small amounts of information, also referred to as a small or smaller payload communications, such as when an IMD is conveying an alert to an external device or when an external device may be downloading a command to direct the IMD to change an operation (e.g., switch to a different pacing mode, change one or more pacing parameters and the like). Software update communications include a relatively large amount of information, also referred to as large or larger payload communications, that is downloaded to the IMD. For example, a software update (including firmware updates) may modify, add, or replace a therapy algorithm, detection algorithm, and the like. The large payload communications may also include data transfers, such as when uploading large amounts of data from the IMD to the external device. For example, a data transfer may involve transfer of EGM signals stored over a period of time, along with data markers and other analytics identified by the IMD.

At 414, the one or more processors of the host determine whether the current communication type represents a small payload (e.g., an alert or command type communication) and if so, flow moves to 416. Otherwise, flow moves to 422.

At 416, the one or more processors of the host set the PHY to be utilized during the transmit and receive operations to a second PHY that is deemed well-suited for the alert/command type communications. In the present example, the second PHY is set to correspond to the LE coded PHY and is set with S=8. At 418, the transceiver of the host changes to the second PHY and the corresponding data rate. In the present example, the transceiver switches to maintain a data rate of 125 Kb/s at the LE coded S8 PHY.

At 420, the host and the slave exchange additional information to establish a communications session. The operations at 416-420 may include the exchange of the various PDU discussed above in connection with setting the PHY at 406, changing the data rate at 408 and establishing a connection at 410.

Returning to 414, when flow moves to 422, the one or processors of the host determine whether the type of communication corresponds to a software update, such as a firmware download. When the communication corresponds to a software update, flow branches to 424. Otherwise, flow continues to 430.

At 424, the one or more processors of the host set the PHY to be utilized during the transmit and receive operations to a third PHY that is deemed well-suited for the software update type communications. In the present example, the third PHY is set to correspond to the LE 2M PHY. At 426, the transceiver of the host changes to the third PHY and the corresponding data rate. In the present example, the transceiver switches to maintain a data rate of 2 Mb/s at the LE 2M PHY. At 428, the host and the slave exchange additional information to establish a communications session. The operations at 424-428 may include the exchange of the various PDU discussed above in connection with setting the PHY at 406, changing the data rate at 408 and establishing a connection at 410.

Returning to 422, when the flow moves to 430, the process has determined that the communication does not relate to an alert or command, nor a software update. Accordingly, the one or more processors of the host determine the size of a data transfer to occur during the communication.

At 432, the one or more processors of the host determine whether the size of the data transfer exceeds or falls below a threshold, and based thereon flow branches to 424 or 434. For example, the communication may correspond to uploading ECG signals (saved in the IMD) to the external device in combination with event markers and other analytics determined by the IMD. When ECG signals and related markers/analytics are to be uploaded, the size of the data transfer is considered to be relatively large, and would exceed the threshold at 432, thereby directing flow to 424. As noted above, at 424, the one or more processors utilize the LE 2M PHY and the data rate of 2 Mb per second. Alternatively, the size of the data transfer may be much smaller, such as when limited results of ECG analysis are to be uploaded. For example, an IMD may simply upload a level of burden associated with an arrhythmia of interest, a battery level, and the like. When a smaller amount of data is to be transmitted, flow moves from 432 to 434. At 434, the one or more processors of the host set the PHY to the third PHY, but set the encoding to a different encoding level, such as the LE coded PHY while utilizing S2 encoding. At 436, the transceiver of the host changes to the third PHY level and the corresponding data rate. In the present example the transceiver switches to maintain a data rate of 500 Kb/s. At 438, the host and the slave exchange additional information to establish a communication session. The operations at 434-438 may include the exchange of the various PDU discussed above in connection with setting the PHY at 406, changing the data rate at 408 and establishing a connection at 410.

As explained in accordance with the process of FIG. 4, when the external device (e.g., programmer) first detects an advertisement notice from the IMD, the external device determines what version of the Bluetooth wireless communication standard is implemented by the IMD. If the IMD uses a transceiver configured in accordance with a Bluetooth standard less than 5.0, then the external device will establish a communication session with the IMD utilizing the single PHY associated with older Bluetooth standards, namely the LE 1M PHY (as that is the only PHY supported by the IMD). The LE 1M PHY only supports a 1 Mb/s data rate for connection. If, however, the IMD includes a transceiver configured to utilize a Bluetooth 5.0 or above standard, then the next step is to determine the purpose of the communication session. If an alert message needs to be sent from the IMD to the external device or a command needs to be sent from the external device to the IMD, the lowest data rate can be applied as this type of transaction is not data heavy. The external device will connect using the LE Coded 8S PHY with the data rate set to 125 Kb/s. If a more substantial transmission such as a firmware download or data transfer was needed, then the programmer would need to identify whether a low data rate or high data rate should be used. For a firmware download and a large data transfer, the highest data rate would be used. The external device would connect using LE 2M PHY with 2 Mb/s data rate. Alternatively, if the amount of data transferred is relatively low, then a lower data rate of 500 Kb/s with an LE Coded 2S PHY can be used.

It should be recognized that while the flowchart in FIG. 4 illustrates what an initial connection might look like, this process also allows for the host to dynamically change the PHY and data rate settings dynamically during a communication session. For example, the decisions and branches of FIG. 4 may be applied during a communication session. If the data payload is heavier than expected, the programmer can switch to a higher data rate to speed up the data transfer. Alternatively, if the communication session is suffering from interference or loss of connection, the programmer can switch to a lower data rate to strengthen the connection at the cost of longer session duration. Lastly, if battery capacity is a constraint, lower data rates can be used to save on current consumption.

Figure 5:
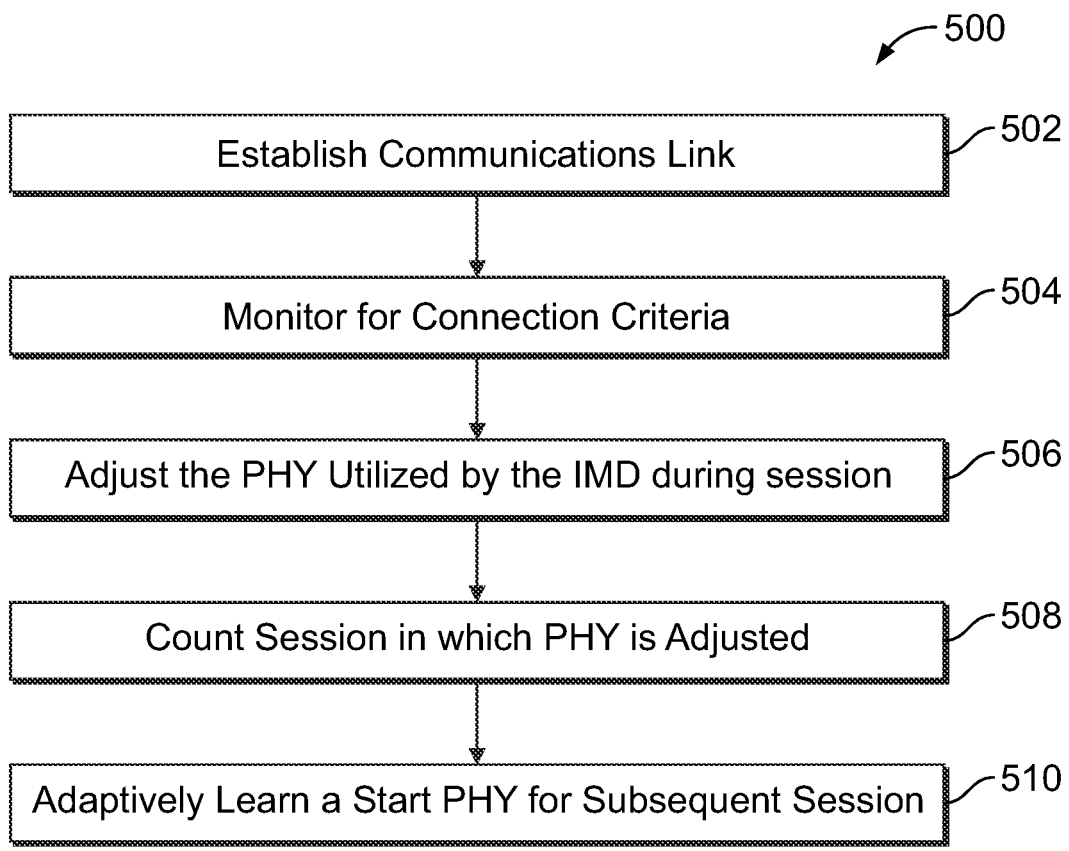
FIG. 5 thus illustrates a flow block diagram of a method for managing selection of the physical layer during a communication session between an external device and an IMD in accordance with one embodiment.

FIG. 5 thus illustrates a flow block diagram of an alternative method for managing change of the physical layer during a communication session between an external device and an IMD. The method may be implemented by hardware components, software components, and/or a combination of hardware components and software components working together to implement the method.

At 502, one or more processors of the IMD and ED establish a communications link, utilizing a desired physical layer that may be chosen in various manners. For example, the initial physical layer or combination of layers may be chosen in accordance with the process of FIG. 4. Alternatively, the initial physical layer may be predetermined based on prior communication sessions. For example, the external device and IMD may be preprogrammed to begin all communication sessions with the physical layer available in the Bluetooth standard version 4.0 (e.g., LE 1M PHY).

At 504, one or more processors monitor connection criteria during the current session, such as one or more of telemetry break condition, a data throughput requirement, a battery indicator, a communication type or a link condition. In one example, the connection criteria correspond to a telemetry break condition that is an actual break where communication is lost for a predetermined interval and must be restored or reestablished. The predetermined interval may be a second, less than a second, more than a minute, and the like. In another example, the telemetry break condition is a potential telemetry break. The potential telemetry break is determined based on measured parameters such as signal strength, interference noise level, signal to noise ratio, and the like. In one example a threshold is provided related to one of these parameters, such as signal to noise ratio, that once exceeded, or once falling below the threshold indicates the potential telemetry break is presented. In one example monitoring the telemetry break condition includes determining a number of return errors from sent data packets. In another example, monitoring includes determining the number of bad packets received by the IMD and/or ED. As another example, the connection criteria may include a change in the type of communication, such as a transition from a low/small payload communication (e.g., an alert or command) to a high/large payload communication (e.g., transferring EGM data from the IMD to the external device). As another example, the connection criteria may include a change from a larger payload communication to a smaller payload communication. For example, a communication session may begin by downloading a software change, firmware update or other higher payload communication, in connection with which a higher data rate physical layer (e.g., LE 2M) may be used. Once the software change or firmware update is completed it may be desirable to continue a communication session but with a low/small payload communication, such as to confirm the operation of the software change or firmware update. When switching to a lower payload communication, the PHY may switch to the LE Coded 2S or 8S PHY (e.g., while a series of tests are implemented to confirm the operation of the software change or firmware update, in which commands are sent from the external device to the IMD and responses are returned).

At 506, one or more processors adjust the PHY utilized by the IMD and ED between small and large payload PHY, during the current session based on the connection criteria. In one example the PHY is changed when a pre-existing condition occurs, such as to increase the data rate from a higher data rate to a lower data rate during a current session in response to a telemetry break, and increase the demand and data throughput or another change in connection criteria. Alternatively, the PHY may be changed from a lower data rate to a higher data rate during a current session when the signal to noise ratio rises above a threshold level during a current session, or a change in the data throughput increases.

At 508, one or more processors increments a count of a number of communications sessions that utilized the current PHY(s). In one example, when the one or more processors determine an in-session PHY transition occurs from the higher data rate to a lower data rate, and in response thereto, the one or more processors increment the count of the number of sessions in which the IMD utilized the LE 1M or LE Coded PHY that support lower data rates. The increment can be represented by a numerical value, such as one, another numerical value, or the like. The one or more processors optionally can determine if the count of the number of sessions in which the IMD utilized the lower data rate has reached a threshold value; and in response to reaching the threshold value, defined the starting PHY for the next communication session to correspond to the PHY that supports the lower data rate (e.g., starting with the LE coded 2S PHY). Different measured events may result in the same result to the count, such as adding one to a count, or may result in a different result to the count.

At 510, the one or more processors adaptively learn a PHY level to be utilized to initiate a next session or certain types of sessions following the current session based on the counting of the number of sessions. In one example, the one or more processors keep track of the count at 508 and when the count reaches a threshold level, then when a next session begins the one or more processors automatically provide a lower data rate PHY to start the next session. Optionally, when a non-telemetry break condition includes determining no return errors or bad packets were received by the IMD during the session, the count may be decremented. In yet another example, multiple iterations of counts can occur. Specifically, a first count may provide the amount of times a telemetry break or other connection criteria occurs during sessions while a second count may provide the amount of times a signal to noise ratio or other connection criteria is below a threshold. By keeping track of the count of predetermined events that indicate the interference level in a known environment, the one or more processors are able to adaptively determine the start PHY for a given environment and given data demand while keeping power usage low for other environments and uses. Thus, the power usage (e.g., associated with the LE 2M PHY) does not need to remain elevated at times when the elevated power level is unneeded (e.g., associated with the LE 1M PHY). Consequently, power is saved, increasing battery life.

Thus, by utilizing the methodologies herein numerous advantages over other systems and methods are achieved. By utilizing a preferred PHY during communication sessions, a better user experience results including having a more robust communication link, more immunity to ambient interferences, and experience fewer interruptions to the link. By utilizing PHY and power switching, the system and methodology allows the device to switch to lower power when the link quality is good or when a communication session is not active. Consequently, power consumption is decreased, resulting in increased IMD life.

While the foregoing embodiments are described in connection with the Bluetooth communications protocol, it is recognized that embodiments herein may be implemented in connection with other communications protocols that have multiple physical layers, where the multiple physical layers have different corresponding data rates, error detection or connection capabilities, signal qualities, power requirements and the like.

CLOSING STATEMENT

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD), comprising:
    a transceiver configured to communicate wirelessly, with an external device (ED), utilizing a protocol that utilizes multiple physical layers;
    the transceiver configured to transmit information indicating that the transceiver is configured with first and second physical layers (PHYs) for wireless communication;
    memory configured to store program instructions;
    one or more processors configured to execute instructions to:
        obtain an instruction designating one of the first and second PHY to be utilized for at least one of transmission or reception, during a communication session, with the external device, wherein the first PHY is the one designated based on connection criteria for a communications link, wherein the connection criteria include at least one of a data throughput requirement, a communication type, a size of data set to be transferred, a battery indicator, a telemetry break condition or link condition of the communications link between the IMD and ED;
        manage the transceiver to utilize, during the communications link, the first as designated; and
        change to the second PHY, while maintaining the communications link, based on a change in the connection criteria.

2. The IMD of claim 1, wherein the transceiver is configured to transmit a communications packet represents at least one of an advertisement packet, a scan request packet or a scan response packet, the communications packet including the information indicating that the transceiver is configured with the first and second PHYs.

3. The IMD of claim 1, wherein the transceiver is configured to receive an ED communications packet from the external device, the ED communications packet including the instruction designating the one of the first and second PHY.

4. The IMD of claim 1, wherein the one or more processors are configured to designate the one of the first and second PHYs by at least one of 1) determining the type of communication or 2) determining the size of data set to be transferred between the ED and IMD, the one or more processors configured to generate the instruction designating the one of the first and second PHYs based on at least one of the type of communication or the size of the data set, at least one of the type of communication or the size of the data set representing the connection criteria.

5. The IMD of claim 1, wherein the protocol corresponds to a Bluetooth protocol, the first and second PHY corresponding to two of LE 1M, LE 2M and LE Coded PHYs, respectively, and the instruction designates the LE 2M PHY when the connection criteria corresponds to a large payload communication.

6. The IMD of claim 1, wherein the instruction designates the LE Coded PHY when the connection criteria corresponds to a small payload communication.

7. The IMD of claim 1, wherein the one or more processors are configured to manage a receiver of the transceiver to utilize the first PHY in connection with receiving communications packets from the ED and to manage a transmitter of the transceiver to utilize the second PHY in connection with transmitting communications packets to the ED.

8. The IMD of claim 1, wherein the one or more processors are further configured to:
    initiate a communications link utilizing the first PHY;
    monitor the connection criteria during the communications link;
    detect the change in the connection criteria; and
    while maintaining the communications link, change from the first PHY to the second PHY based on the change in the connection criteria.

9. The IMD of claim 1, wherein the first and second PHY have at least one of different data rates or error detection capabilities.

10. An external device (ED) configured to wirelessly communicate with an implantable medical device (IMD) utilizing a protocol that supports multiple physical layers (PHYs), the ED comprising:
    an external transceiver configured to wirelessly communicate with the IMD;
    the external transceiver configured to receive a communications packet;
    memory configured to store program instructions;
    one or more processors that are configured, when implementing the program instructions, to:
        analyze the communications packet for information indicating whether the IMD is configured with multiple physical layers (PHYs) for wireless communication;
        select one of the multiple PHYs based on connection criteria for a communications link, wherein the connection criteria include at least one of a data throughput requirement, a communication type, a size of data set to be transferred, a battery indicator, a telemetry break condition or link condition of the communications link between the IMD and ED;

transmit an instruction to the IMD to utilize the one of the multiple PHYs selected for at least one of transmission or reception during the communications link; and change to another of the multiple PHY, while maintaining the communications link, based on a change in the connection criteria.

11. The device of claim 10, wherein the one or more processors are further configured to receive, as the communications packet, an advertisement packet, and analyze a content of the advertisement packet for the information indicating where the IMD is configured with the multiple PHYs.

12. The device of claim 10, wherein the information analyzed from the communications packet indicates whether the IMD is compatible with Bluetooth version 5.0 or higher.

13. The device of claim 10, wherein the connection criteria include a type of the communication and wherein the one or more processors are configured to determine the type of communication and select between a first and a second PHY from the multiple PHYs based on the type of communication.

14. The device of claim 10, wherein, following the select and transmit operations, the one or more processors are configured to manage the external transceiver to establish the communications link with the IMD utilizing the one of the multiple PHYs.

15. The device of claim 10, wherein the one or more processors are configured to enter a connection state to initiate the communications link utilizing a first PHY from the multiple PHY and, to change, during the communications link while in the connection state, to a second PHY from the multiple PHY based on the change in the connection criteria.

16. The device of claim 10, wherein the multiple PHYs have at least one of different data rates or error detection capabilities.

17. An external device (ED) configured to wirelessly communicate with an implantable medical device (IMD) utilizing a protocol that supports multiple physical layers (PHYs), the ED comprising:

an external transceiver configured to wirelessly communicate with the IMD;

the external transceiver configured to receive a communications packet;

memory configured to store program instructions;

one or more processors that are configured, when implementing the program instructions, to:

analyze the communications packet for information indicating whether the IMD is configured with multiple physical layers (PHYs) for wireless communication;

select one of the multiple PHYs based on connection criteria for a communications link; and transmit an instruction to the IMD to utilize the one of the multiple PHYs selected for at least one of transmission or reception during the communications link, wherein the connection criteria include a size of a data set and wherein the one or more processors are configured to determine the size of the data set to be transferred and select between a first PHY and a second PHY from the multiple PHYs based on the size of the data set to be transferred.

18. A method for managing a wireless communication between an external device (ED) and an implantable medical device (IMD) utilizing a protocol that supports multiple physical layers (PHYs), the multiple PHY having at least one of different data rates or error detection capabilities, the method comprising:

selecting, at one of the ED or IMD, one of the multiple PHYs for wireless communication based on a connection criteria for a communications link, wherein the connection criteria include at least one of a data throughput requirement, a communication type, a size of data set to be transferred, a battery indicator, a telemetry break condition or link condition of the communications link between the IMD and ED; and transmitting an instruction, to another of the ED or IMD, to utilize the one of the multiple PHYs selected for at least one of transmission or reception during the communications link; and changing to another of the multiple PHY, while maintaining the communications link, based on a change in the connection criteria.

19. The method of claim 18, further comprising receiving, at the ED, a communications packet from the IMD; and analyzing the communications packet for information indicating whether the IMD is configured with multiple physical layers (PHYs) for wireless communication, the ED performing the selecting the one of the multiple PHYs and transmitting the instruction to the IMD.

20. The method of claim 18, further comprising collecting and analyzing the connection criteria.

21. The method of claim 18, further comprising determining, as the connection criteria, at least one of 1) the type of communication or 2) the size of the data set to be transferred, and based thereon selecting the one of the multiple PHYs.

22. The method of claim 18, further comprising establishing the communications link between the ED and the IMD utilizing the one of the multiple PHYs.

23. The method of claim 18, further comprising entering a connection state to initiate the communications link utilizing a first PHY from the multiple PHY and, changing, during the communications link while in the connection state, to a second PHY from the multiple PHY based on the change in the connection criteria.

* * * * *